United States Patent
Ganem et al.

(10) Patent No.: US 8,506,632 B2
(45) Date of Patent: Aug. 13, 2013

(54) INTERVERTEBRAL IMPLANT INTENDED TO ALLOW IMMOBILIZATION OF ONE VERTEBRA IN RELATION TO ANOTHER

(75) Inventors: Franck Ganem, Caen (FR); Alexis Faline, Collonges au Mont d'Or (FR); Pierre Bernard, Merignac (FR); Vincent Fiere, Lyons (FR)

(73) Assignee: Medicrea International, Neyron (FR)

( * ) Notice: Subject to any disclaimer, the term of this patent is extended or adjusted under 35 U.S.C. 154(b) by 83 days.

(21) Appl. No.: 12/991,241

(22) PCT Filed: May 27, 2009

(86) PCT No.: PCT/IB2009/052216
§ 371 (c)(1),
(2), (4) Date: Feb. 7, 2011

(87) PCT Pub. No.: WO2009/144671
PCT Pub. Date: Dec. 3, 2009

(65) Prior Publication Data
US 2011/0172769 A1    Jul. 14, 2011

(30) Foreign Application Priority Data
May 27, 2008   (FR) ...................... 08 02864

(51) Int. Cl.
*A61F 2/44*    (2006.01)
(52) U.S. Cl.
USPC .................................... 623/17.11; 623/17.16
(58) Field of Classification Search
USPC ............ 606/246, 248, 249; 623/17.11–17.16
See application file for complete search history.

(56) References Cited

U.S. PATENT DOCUMENTS

| | | | |
|---|---|---|---|
| 8,002,837 B2 * | 8/2011 | Stream et al. | 623/17.16 |
| 2005/0149195 A1 * | 7/2005 | Boyd et al. | 623/17.11 |
| 2006/0167548 A1 | 7/2006 | Jackson | |

FOREIGN PATENT DOCUMENTS

| | | |
|---|---|---|
| EP | 0 042 271 A1 | 12/1981 |
| EP | 0 307 241 A2 | 3/1989 |
| WO | WO 2004/089259 A1 | 10/2004 |

OTHER PUBLICATIONS

Written Opinion issued in corresponding PCT Application No. PCT/IB2009/052216, mailed Oct. 9, 2009.
International Search Report issued in corresponding PCT Application No. PCT/IB2009/052216, mailed Oct. 9, 2009.

* cited by examiner

*Primary Examiner* — Eduardo C Robert
*Assistant Examiner* — Christina Negrellirodriguez
(74) *Attorney, Agent, or Firm* — Oliff & Berridge, PLC

(57) ABSTRACT

An implant that allows immobilization of one vertebra in relation to another, having two lateral walls essentially parallel one with respect to the other and having a length, and at least one transverse wall connecting these lateral walls one to the other, at least one of these lateral walls having, on its side facing the side opposite the other lateral wall, slide prevention reliefs. The invention, the implant has, in a direction perpendicular to the length of the lateral walls, a dimension such that its two lateral walls are capable of coming into the immediate vicinity of the unci of the underlying vertebrae, the slide prevention reliefs of each of lateral wall thus being able to bear against the internal surface of the uncus of the underlying vertebra adjacent this lateral wall.

10 Claims, 2 Drawing Sheets

INTERVERTEBRAL IMPLANT INTENDED TO ALLOW IMMOBILIZATION OF ONE VERTEBRA IN RELATION TO ANOTHER

The present invention concerns an intervertebral implant intended to allow immobilization of one vertebra in relation to another. This implant can be used in particular to immobilize two cervical vertebrae.

It is well known to immobilize two vertebrae in relation to each other using an intervertebral implant in a stiff material, making it possible to reestablish suitable spacing of the vertebrae. The implant can form a cage which defines a housing designed to receive one or several bone grafts and/or cancellous bone chips, the implant then making it possible to prevent crushing of the graft by the vertebrae. The immobilization of the vertebrae in relation to the implant is done by growth of bone cells through the graft(s) and/or chip(s), leading to what is commonly called a "fusion" of two vertebrae.

Some intervertebral implants have a reduced width, allowing their placement from the rear, on either side of the spinal cord. It is then necessary to place two implants, one on the left side of the spinal cord and the other on the right side. Document EP 0 042 271 describes an implant of this type.

This technique has the drawbacks of being relatively risky to implement, involving piercing holes near the spinal cord and requiring the use of implants with a reduced width, allowing only a small contact surface of the grafts with the vertebrae. In addition, this technique is not usable on cervical vertebrae, given the reduced dimensions of these vertebrae, which does not allow the placement of two implants, and the configuration of these vertebrae on their posterior side.

To resolve these drawbacks, it is common to place an intervertebral implant from the front. This approach being larger than the rear, an implant of this type can have a shape such that it extends over a significant portion of the surface of a vertebral plate, and can therefore contain one or several grafts having a significant contact surface with the vertebral plates, which is an essential condition for the success of the vertebral fusion. An implant of this type generally comprises a peripheral wall defining the housing for receiving the graft.

This type of implant, widely used in practice, is not, however, fully satisfactory. Indeed, many existing implants have notable risks of insertion in one and/or the other of the vertebral plates, and/or risks of expulsion under the effect of repeated stresses transmitted by the vertebrae. These risks exist in particular regarding cervical vertebrae, given the reduced dimensions of the implant and the repeated movements of these vertebrae.

The present invention aims to resolve these essential drawbacks.

The concerned implant comprises, in a known manner, two lateral walls essentially parallel one with respect to the other and having a length, and at least one transverse wall connecting these lateral wall one to the other, at least one of these lateral walls having, on its side facing the side opposite the other lateral wall, slide prevention reliefs.

According to the invention, the implant has, in a direction perpendicular to said length of the lateral walls, a dimension such that said two lateral walls are capable of coming into the immediate vicinity of the unci of the underlying vertebrae, the slide prevention reliefs of each of said lateral wall thus being able to bear against the internal surface of the uncus of the underlying vertebra adjacent this lateral wall.

The implant according to the invention thus has a maximum width, allowing a maximum contact surface with the vertebrae and stabilization of these vertebrae. It then has a larger contact surface with the vertebral plates, which increases its resistance to insertion into one or the other of the vertebral plates. The implant comprises lateral slide prevention reliefs able to bear against the internal surface of an uncus of the underlying vertebra, i.e. against the bone rib which the plate of this vertebra presents laterally; this bearing makes it possible to effectively present an obstacle to the sliding of said lateral wall along this uncus, and therefore to effectively oppose the risk of expulsion of the implant, particularly when this implant is placed between the cervical vertebrae.

Preferably, said lateral wall has, on its side facing the side opposite the other lateral wall, an inclined flank allowing this lateral wall, after implantation, in the immediate vicinity of the internal surface of the uncus of the underlying vertebra.

The shape of said lateral wall is thus adapted to that of the uncus and allows bearing of said slide prevention reliefs on an extended area of the internal surface of the uncus.

Preferably, each of the two lateral walls has slide prevention reliefs and an inclined flank as previously mentioned.

In this way, the implant is perfectly maintained in relation to the vertebrae.

Said inclined flank defines, with the surface of said lateral wall facing the other lateral wall, a support surface of this lateral wall intended to come up against the underlying vertebra. Preferably, this inclined flank is arranged such that this support surface intended to come up against the underlying vertebra is reduced to an edge.

This edge is capable of biting more or less into the vertebral plate of the underlying vertebra and, jointly with said slide prevention reliefs, ensures effective prevention of the risk of expulsion of the implant.

Preferably, said inclined flank connects to said edge via a convex rounded surface.

This rounded surface allows, in case of beginning of insertion of the implant into the plate of the underlying vertebra, a quick increase of the support surface of the implant against this plate, and therefore effective prevention of the continuation of this insertion.

Preferably, said slide prevention reliefs are realized in the form of a series of ribs side by side formed by a series of channels arranged side by side.

These reliefs, thus configured, effectively oppose the sliding of the implant along an uncus of the underlying vertebra.

To this same end, the ribs can have sharp terminal edges.

Advantageously, said ribs continue to said convex rounded surface, up to the edge constituting said support surface intended to come up against the underlying vertebra.

The surface occupied by the slide prevention reliefs thus extends to said convex rounded surface and is therefore significant. Moreover, said ribs and channels grant this edge a scalloped form, or the shape of a series of protruding teeth, which ensures very effective support of the implant in the plate of the underlying vertebra and prevents any expulsion of the implant.

Preferably, the implant comprises two transverse walls, one anterior and one posterior, connecting said lateral walls, and defines an internal space for receiving one or several bone grafts and/or cancellous bone chips.

The invention will be well understood, and other characteristics and advantages thereof will appear, in reference to the appended diagrammatic drawing, illustrating, as a non-limiting example, one preferred embodiment of the intervertebral implant it concerns.

Figure 4:
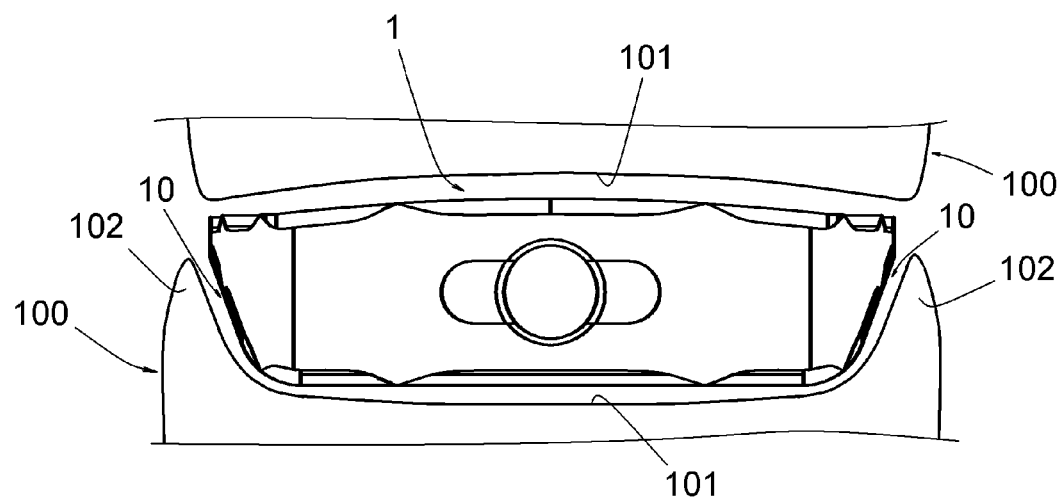
FIG. 4 is a side view, after placement between the vertebral plates of two vertebrae.

The figures illustrate an intervertebral implant 1 intended to enable immobilization of one vertebra in relation to another, in particular immobilization of two cervical vertebrae. As shown by FIG. 4, this implant 1 is intended to be inserted between the vertebral plates 101 of two vertebrae 100 and to assume a position between the unci 102 of the underlying vertebra 100, i.e. the bone ribs presented laterally by the plate 101 of this vertebra.

Figure 1:
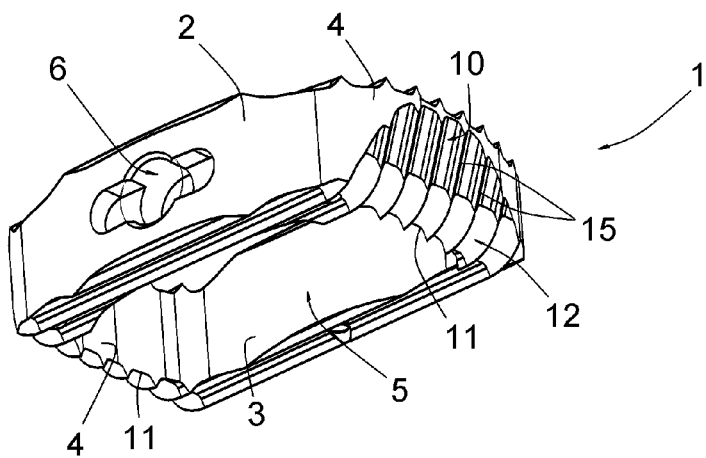
FIG. 1 is a perspective view.
Figure 2:
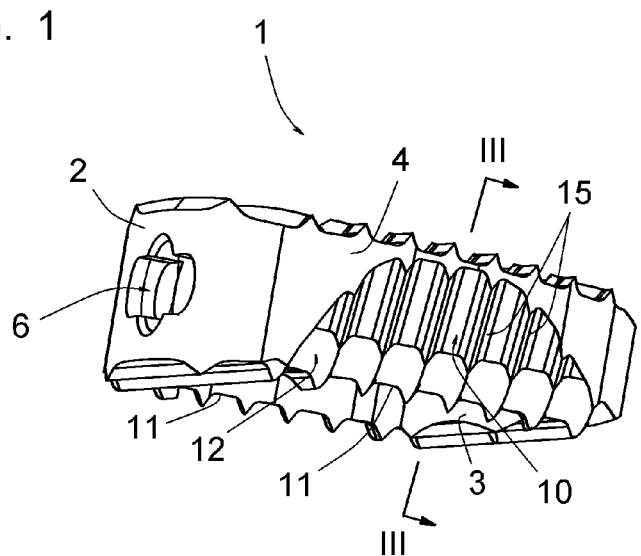
FIG. 2 is also a perspective view, from a different angle.
Figure 3:
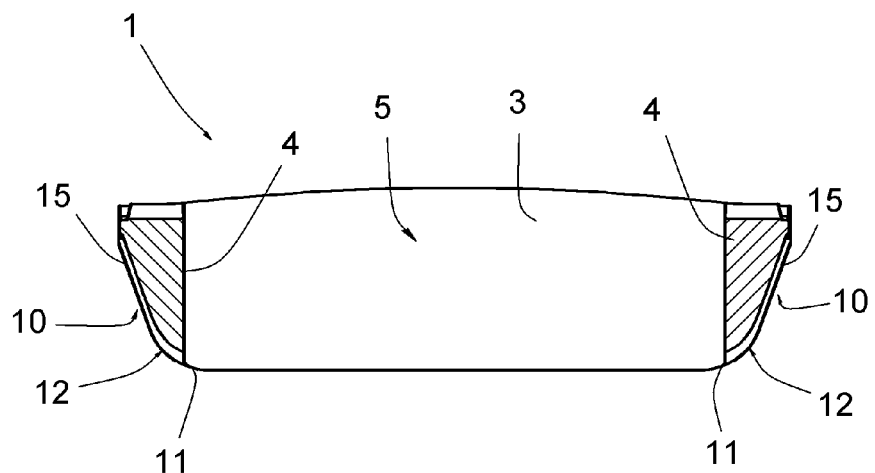
FIG. 3 is a cross-sectional view along line III-III of FIG. 2.

In reference to FIGS. 1 to 3, it appears that the implant 1 comprises an anterior transverse wall 2, a posterior transverse wall 3 and two lateral walls 4. These different walls 2 to 4 form bodies and define an internal space 5 between them for receiving one or several bone grafts and/or cancellous bone chips.

The anterior wall 2 comprises, traditionally, a mark 6 for mounting the implant 1 on a tool (not shown) for impacting the implant between the vertebrae 100.

Each lateral wall 4 has, on its side facing the side opposite the other lateral wall 4, an inclined flank 10, such that the support surface intended to come up against the underlying vertebra 100 is reduced to an edge 11, as shown by FIG. 3.

The inclined flank 10 connects to this edge 11 by a convex rounded surface 12.

Each lateral wall 4 also has slide prevention reliefs, able to bear against an uncus of the underlying vertebra 100. These reliefs are realized in the form of a series of ribs 15 side by side, formed by a series of channels arranged side by side, from the outer surface of the wall 4. The ribs 15 and channels extend over the inclined flanks and continue to the convex rounded surface 12, up to the edge 11, such that they grant this edge 11 a scalloped shape, or with a series of protruding teeth, as appears in FIGS. 1 and 2.

The channels are arranged immediately next to each other, such that the ribs 15 have sharp terminal edges.

As shown by FIG. 4, the inclined flanks 10 allow the implant 1 to come as close as possible to the unci 102 of the underlying vertebra 100 and to bear against the internal surfaces of these unci 102 via the ribs 15. The latter parts, by their terminal sharp edges, effectively prevent the sliding of the implant 1 along these unci 102, and therefore the risk of expulsion of the implant.

Moreover, the edges 11 bite more or less into the vertebral plate of the underlying vertebra 100, due to the scalloped shape they have. Jointly with the ribs 15, they contribute to ensuring effective prevention of the risk of expulsion of the implant.

The risk of insertion of the implant in the plate of the underlying vertebra 100 remains limited, however, given that the rounded surfaces 12 allow, in case of beginning of insertion, a quick increase of the support surface of the implant 1 against this plate, and therefore effective prevention of the continuation of this insertion.

The risk of insertion of the implant into the plate of the underlying vertebra 100 remains limited, however, due to the fact that the upper support surfaces formed by the walls 4 retain a significant area.

The implant 1 also has a significant width and therefore has a larger contact surface with the vertebral plates, which contributes to increasing the resistance of the implant to an insertion in one or the other of the vertebral plates and provides the graft and/or bone chips with a significant contact surface with the vertebral plates.

As appears from the preceding, the invention provides an intervertebral implant having the determining advantages of having a low risk of expulsion and a low insertion risk, and being particularly suited to placement between cervical vertebrae.

The invention was described above in reference to embodiments provided purely as examples. It goes without saying that it is not limited to these embodiments, but that it extends to all embodiments covered by the appended claims.

The invention claimed is:

1. An intervertebral implant, capable of allowing immobilization of one vertebra in relation to another vertebra, the vertebrae having respective vertebral plates, the implant comprising:
    two lateral walls essentially parallel to each other;
    the lateral walls being, when the implant is positioned between the vertebrae, perpendicular to the respective vertebral plates;
    at least one transverse wall connecting the lateral walls to each other;
    a dimension of the at least one transverse wall being wide enough to place the lateral walls immediately adjacent to unci of an underlying vertebrae on which the implant is positioned;
    at least one of the lateral walls having slide prevention reliefs facing outward; and
    the slide prevention reliefs being configured to bear against an internal surface of the uncus of the underlying vertebra adjacent to the at least one lateral wall,
    said at least one lateral wall has an inclined flank allowing said lateral wall, after implantation, to come immediately adjacent to the internal surface of the uncus of the underlying vertebra, the inclined flank having the slide prevention reliefs disposed thereon in the form of ribs that extend perpendicularly to a length of the at least one lateral wall.

2. The intervertebral implant according to claim 1, wherein each of the two lateral walls has the slide prevention reliefs and the inclined flank.

3. The intervertebral implant according to claim 1, wherein said inclined flank defines a support surface of the lateral wall configured to contact the underlying vertebra, and the inclined flank is arranged such that the support surface is reduced to an edge.

4. The intervertebral implant according to claim 3, wherein said inclined flank connects to said edge via a convex rounded surface.

5. The intervertebral implant according to claim 1, wherein the slide prevention reliefs include a series of ribs side by side formed by a series of channels arranged side by side.

6. The intervertebral implant according to claim 5, wherein said ribs have sharp terminal edges.

7. The intervertebral implant according to claim 6, wherein said ribs continue to said convex rounded surface, up to an edge.

8. The intervertebral implant according to claim 5, wherein said ribs continue via a convex rounded surface up to an edge.

9. The intervertebral implant according to claim 5, wherein said ribs continue to said convex rounded surface, up to an edge.

10. The intervertebral implant according to claim 1, comprising two of the transverse walls, one anterior and one posterior, connecting said lateral walls, and defining an internal space for receiving at least one bone graft and/or cancellous bone chip.

* * * * *